United States Patent [19]

Wildman

[11] Patent Number: 5,094,614
[45] Date of Patent: Mar. 10, 1992

[54] MINIATURE SELF-LOCKING LABIAL BRACKET

[76] Inventor: Alexander J. Wildman, 2662 Donner Pl., Eugene, Oreg. 97401

[21] Appl. No.: 666,249

[22] Filed: Mar. 8, 1991

[51] Int. Cl.⁵ .............................................. A61C 3/00
[52] U.S. Cl. ........................................ 433/14; 433/10
[58] Field of Search ....................... 433/14, 9, 18, 8, 10

[56] References Cited

U.S. PATENT DOCUMENTS

| | | | |
|---|---|---|---|
| 1,280,628 | 10/1918 | Angle | 433/14 |
| 1,821,171 | 9/1931 | Atkinson | 433/14 |
| 2,671,964 | 3/1954 | Russell et al. | 433/13 |
| 3,085,335 | 4/1963 | Kesling | 433/14 |
| 3,087,244 | 4/1963 | Huettner et al. | 433/14 |
| 3,163,933 | 1/1965 | Begg et al. | 433/14 |
| 3,256,602 | 6/1966 | Broussard et al. | 433/13 |
| 3,262,207 | 7/1966 | Kesling | 433/10 |
| 3,578,744 | 5/1971 | Wildman | 433/14 |
| 3,772,787 | 11/1973 | Hanson | 433/14 |
| 3,780,437 | 12/1973 | Wildman | 433/14 |
| 4,077,126 | 3/1978 | Pletcher | 433/10 |
| 4,103,423 | 8/1978 | Kessel | 433/10 |
| 4,149,314 | 4/1979 | Nonnenmann | 433/10 |
| 4,243,386 | 1/1981 | Kawaguchi | 433/9 |
| 4,248,588 | 2/1981 | Hanson | 433/11 |
| 4,268,249 | 5/1981 | Forster | 433/10 |
| 4,310,306 | 1/1982 | Wallshein | 433/14 |
| 4,419,078 | 12/1983 | Pletcher | 433/10 |
| 4,443,189 | 4/1984 | Wildman | 433/10 |
| 4,492,573 | 1/1985 | Hanson | 433/14 |
| 4,496,318 | 1/1985 | Connelly, Jr. | 433/14 |
| 4,561,844 | 12/1985 | Bates | 433/14 |
| 4,634,662 | 1/1987 | Rosenberg | 433/10 |
| 4,713,001 | 12/1987 | Klein et al. | 433/18 |
| 4,941,825 | 7/1990 | Lerner | 433/14 |

OTHER PUBLICATIONS

Stoller, A. E., *The Universal Appliance*, 1971, pp. 1–26.

*Primary Examiner*—John J. Wilson
*Attorney, Agent, or Firm*—Marger, Johnson, McCollom & Stolowitz, Inc.

[57] ABSTRACT

A bracket having a closure slot extending through both sides of the bracket body across an archwire slot for a closure member to secure an archwire. The bracket body is compact, with a continuous profile, and the closure member ends are contained within the closure slot, so that a collar for an auxiliary attachment can be mounted on the bracket. The bracket body has an internal shoulder extending across one side of the closure slot. The closure member is a lengthwise-folded flat spring having a free end positioned near one end and biased to engage the shoulder when closed. A locking tab cooperates with the free end to lock the closure member closed. Depressing the free end allows it to pass through an escape notch in the internal shoulder to slide the closure member to an open position. Intermediate ears positioned near the opposite end engage the shoulder when open. The free end springs outward to hold the member open. The bracket body has a recessed base to space the archwire slot close to a bonding pad.

27 Claims, 9 Drawing Sheets

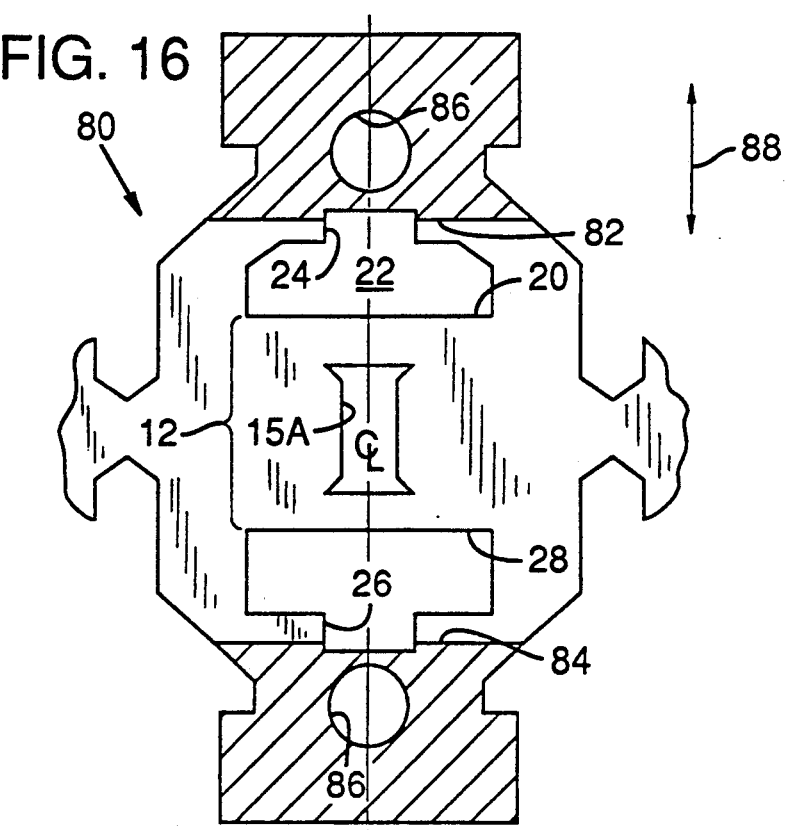
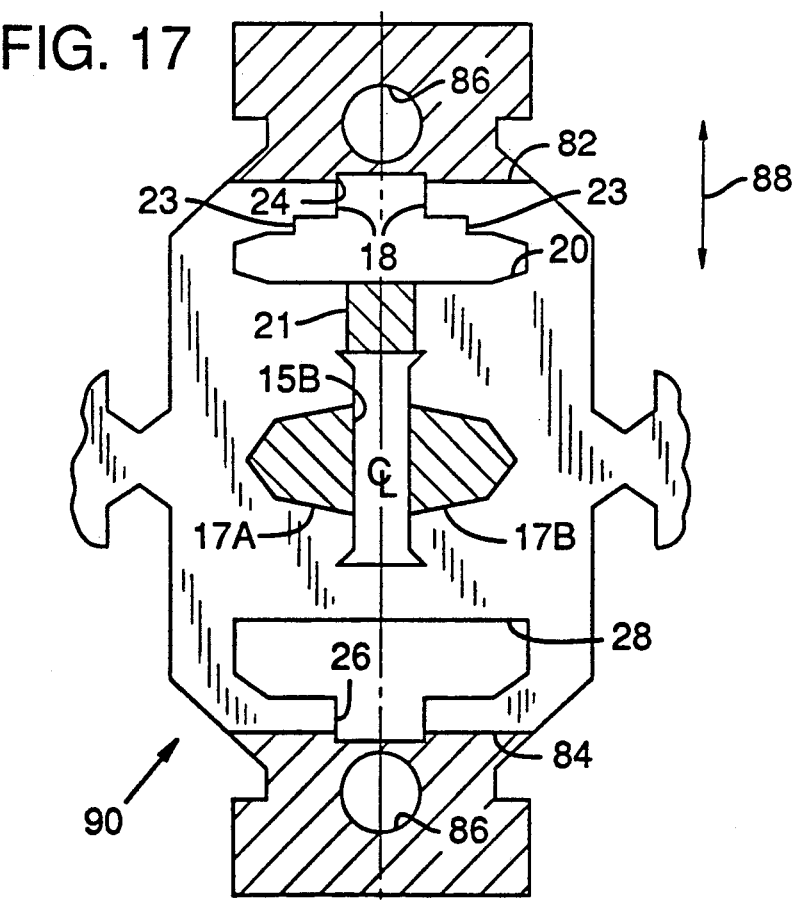

MINIATURE SELF-LOCKING LABIAL BRACKET

BACKGROUND OF THE INVENTION

This invention relates generally to orthodontic attachments and more particularly to a miniature ligatureless or automatic locking-type labial bracket.

BACKGROUND OF INVENTION

Improperly positioned teeth may be moved into an optimum position by force of a flexible wire which orthodontists call an "archwire." This archwire is formed into a shape that will move the teeth to a desired position when the archwire is attached to the teeth. The attachment mechanism is called a bracket. The bracket typically has a slot designed to receive the archwire. Known archwire slots are circular, square or U-shaped channels, depending on the type of archwire and manufacturing constraints. For example, James Reynolds has patented and manufactured ceramic brackets with U-shaped archwire slots to avoid fracture problems. The slot is closed to secure the archwire in the bracket with a closure or locking means.

The most common arrangement, shown in FIG. 1, is a tie-wing bracket. The archwire slot is conventionally oriented for insertion of an archwire in a labiolingual direction, i.e., generally parallel to the occlusal plane. The bracket body has projections or wings 50 which allow the archwire slot to be closed with a twisted wire or an elastomer O-ring 52 that can be pulled around the wings into a tie opening 51 to close the slot. The closure means typically has to be removed each time an archwire is changed. To make this easier, a number of different forms of closure means have been proposed. U.S. Pat. No. 3,256,602 (Broussard) shows a spring-type closure on a wing-type bracket.

Another general type of closure can be referred to as a bail-type closure. U.S. Pat. Nos. 4,077,126 and 4,419,078 (Pletcher) disclose a locking member which include a slotted hollow hub which is rotatable axially about the archwire slot to permit insertion of the archwire and to lock the archwire in place. U.S. Pat. No. 4,103,423 (Kessel) employs a hinged locking hook which has an over center arrangement so that the free end of the locking hook can be hooked over one of the wings of the bracket body across the archwire slot. U.S. Pat. No. 4,149,314 (Nonnenmann) discloses a spring-type bail which extends over the archwire slot and passes over opposite latching wings. U.S. Pat. No. 4,634,662 discloses a locking mechanism which incorporates a slidable, tapered and rotatable plug with an attached lever system for contacting and seeding an archwire in the archwire slot. Besides adding to the complexity of the basic orthodontic bracket, these forms of closure means do not rigidly control the archwire which, in this type of bracket, is inserted in a direction generally parallel to the occlusal plane.

Another basic type of bracket has an archwire slot oriented so that the direction of insertion of an archwire is normal to the occlusal plane. This type of bracket conventionally uses a pin-type closure means such as is disclosed in U.S. Pat. No. 1,280,628 (Angle); U.S. Pat. Nos. 3,085,335 and 3,262,207 (Kesling), and U.S. Pat. No. 3,163,933 (Begg et al.). In general, these forms of brackets provide less control of the archwire than the edgewise-type brackets of FIG. 1 and the patents cited in the preceding paragraphs. One attempt to improve upon conventional pin-type brackets is disclosed in U.S. Pat. No. 4,496,318 (Connelly, Jr.) and takes the form of an insert member which includes an archwire slot and a wing so as to convert a pin-type bracket to a wing-type bracket.

Another variation, disclosed in U.S. Pat. No. 4,268,249 (Forster) and U.S. Pat. No. 4,561,844 (Bates), each disclose a rotary catch member which rotates about an axis perpendicular to the occlusal plane to position a radial member across the archwire slot. While the latter two designs improve control over conventional pin-type brackets, they sacrifice compactness.

Another type of bracket has a pin-type closure but has two archwire slots, one positioned as in the Angle bracket, the second positioned for labio-lingual insertion and removal, both closable by inciso-gingival insertion of a pin, as shown in U.S. Pat. No. 1,821,171 (Atkinson) and further described in Stooler, A.E., *The Universal Appliance* 1971, pages 1-26.

Other general types of bracket are commonly referred to as ligatureless or automatic brackets. Rather than a tie-wire or O-ring as in the case of edgewise brackets, or a pin as in the case of pin-type brackets, ligatureless brackets are generally characterized by an archwire slot oriented for insertion of the archwire in a direction generally parallel to the occlusal plane and a sliding member which is moved transversely from an open position to a closed position to position one leg of the slider across the archwire slot to secure the archwire therein. In an automatic bracket, the closure member can be readily opened and ordinarily remains connected to the bracket body in an open position.

U.S. Pat. No. 2,671,964 (Russell et al.) discloses a sliding bar with a recess at its distal end for containing the archwire in the archwire slot. Applicant's prior U.S. Pat. Nos. 3,578,744 and 3,780,437 disclose a labial bracket with a U-shaped slider which has been marketed under the trademark EDGELOCK by ORMCO Corporation. Applicant has also designed a lingual bracket, disclosed in U.S. Pat. No. 4,443,189, which operates in generally similar fashion. U.S. Pat. No. 3,772,787 and 4,248,588 (Hanson) disclose a bracket in which the slider member is formed by a generally U-shaped spring. U.S. Pat. No. 3,087,244 (Huettner et al.) discloses a bracket which employs a removable semicircular snap ring received in an annular groove over the archwire slot. This bracket is similar in overall structure but is not an automatic bracket in function because the snap ring is wholly removable.

In general, these brackets are much easier for the orthodontist to use, particularly in changing archwires, and provide more precise control of the archwire. Such devices are very complex, however, and therefore difficult and expensive to manufacture. Also, they are not as compact as would be desired. Additionally, it is difficult to use auxiliary attachments with brackets of this type. The Hanson bracket is more compact than the others of this type but sacrifices strength; that is, the force that can be exerted on the archwire by the distal end of the U-shaped spring-type slider which presses against the archwire. In an attempt to avoid this problem, the commercial version of the Hanson bracket has a receptacle or groove alongside the archwire slot into which the distal end of the slider is received in order to reinforce its holding integrity. This bracket still has a profile unsuited for use with auxiliary attachments.

A general problem with the locking of all current orthodontic brackets is the area of the surface of the bracket used by the locking devices of these brackets. Ideally, the locking device should operate only on the front of the archwire, closing the archwire slot. It would be desirable to construct the bracket so that the locking device operates only in the surface in front of the archwire slot, leaving the sides of the bracket free to receive attachment means such as auxiliary collars which could be used to attach various auxiliary devices.

Accordingly, a need remains for an improved labial orthodontic bracket.

SUMMARY OF THE INVENTION

It is, therefore, an object of the invention to provide an improved automatic or ligatureless labial bracket which is small, strong and easy to use.

A second object is to make an automatic or ligatureless labial bracket which is more compact yet at least as strong as prior automatic brackets.

Another object of the invention is to simplify the structure of automatic or ligatureless labial brackets and to make them less expensive to fabricate.

A further object of the invention is to enable the use of auxiliary attachments on an automatic labial bracket.

The invention is a self-locking orthodontic bracket having several novel aspects. In general, the bracket includes a bracket body, mountable on a tooth, having first and second side portions spaced apart to define an archwire slot for receiving an archwire. The bracket includes a closure slot which extends transversely over the archwire slot in the bracket body and a closure member receivable within the closure slot and slidable across the archwire slot. The closure slot includes a first slot portion formed in the first side portion of the bracket body and a second slot portion formed in the second side portion of the bracket body on opposite sides of the archwire slot. The closure member can thus be slid to a closed position through the first slot portion transversely of the archwire slot with an end portion inserted into the second slot portion to retain the archwire in the archwire slot.

In one aspect of the invention, the bracket body and closure member include first locking means for releasably locking the closure member in said closed position in the closure slot and second locking means for locking the closure member in an open position in the closure slot to insert or remove the archwire.

In a preferred embodiment, the first slot portion includes means defining an internal shoulder oriented normal to the direction of closure of the closure member. The closure member includes a folded flat spring member having a free end biased outward to engage the internal shoulder to define said first locking means when the closure member is in the closed position and an intermediate retention ear positioned to engage the internal shoulder to define said second locking means when the closure member is in the open position. The closure member can further include a flat core member with the flat spring member wrapped lengthwise around the core member. The core member has an end protruding through the spring member and bendable downward to engage an outer side of the bracket body to retain the closure member in the closed position. The bracket preferably includes third, frictional locking means for resisting movement of the closure member from the open to closed positions. This can be provided by the free end of the flat spring member being biased upward against an upper wall of the first slot portion. Also, the free end can be sized to a width narrower than the closure slot and the internal shoulder can include an escape notch for releasing the free end when depressed.

In another aspect of the invention, the closure member and closure slot have a generally flat, rectangular shape. That is, they have a width substantially greater than the thickness thereof and greater than the width of the archwire slot. This shape, preferably implemented in a folded flat spring as mentioned above, can distribute the shear forces of retaining the archwire in the archwire slot over a substantial width of the closure member and improve torsional control.

In a further aspect of the invention, the bracket body has an external profile which is substantially continuous, i.e., unbroken by wings or the like, so that a collar can be slid over it in close proximity around the sides of the bracket body. The closure member is preferably formed with a generally flat, rectangular shape, as aforementioned, and with ends which are positioned substantially flush with the sides of the body when received in the closure slot in the closed position. This enables an auxiliary attachment mounted on a collar closely conforming to the profile of the bracket body to be placed on or removed from the bracket without removing the closure member.

The bracket can be mounted on a bonding pad or band so as to position the archwire slot for insertion of the archwire in either an inciso-gingival direction or a generally labio-lingual direction which can include a range of angles. In the latter case, a central outer portion of the bracket body walls is preferably recessed to receive the pad, thereby positioning the archwire slot close to the pad. The bracket body can have walls of substantially constant thickness formed into a U-shaped cross section to form the side portions that define the archwire slot and the continuous external profile of the body.

Advantages of the foregoing bracket include ease of use by the orthodontist, positive archwire control, and ability to easily add or remove auxiliary attachments. The bracket can be made very small, which is preferred for patient comfort, but with a simple enough structure for ease of manufacture and without such small or complex parts that the orthodontist would have difficulty manipulating it.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 16 and 17 are plan views, to scale, of patterned, unformed inner and outer layers of the preferred embodiment of the body of the bracket of FIG. 2, shading in FIG. 17 indicating half-etched regions.

DETAILED DESCRIPTION

Figure 1:
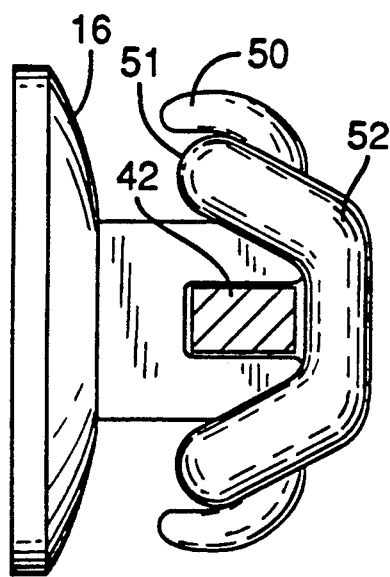
FIG. 1 is an end elevation view, shown to scale, of a conventional winged bracket with an archwire shown in cross section in the archwire slot.

FIGS. 2-7 show a miniature self-locking orthodontic bracket 10 according to a presently-preferred embodiment of the invention. The bracket comprises a bracket body 14 mounted on a pad 16 arranged for mounting on a tooth. The pad can be a foil mesh, perforated or other form of bonding pad concavely formed to fit a convex surface of a tooth, or it can be a band. A recess 17 is formed in the central portion of the bracket body where it contacts the pad, as shown in FIGS. 7-12, thereby positioning the archwire slot close to the pad.

The bracket body has first and second side portions 14A, 14B (see FIGS. 3, 4, 9 and 12) spaced apart to define an archwire slot 12 for receiving an archwire 42. The bracket body has walls of substantially constant thickness formed into a U-shaped cross section to form the side portions that define the archwire slot as well as a continuous external profile of the bracket body. The archwire slot 12 can have a U-shaped profile, as shown, or can have a rectangular profile. The slot is preferably sized for edgewise techniques; that is, its depth is greater than its width for receiving an archwire in an edgewise position.

The bracket body can be positioned on the pad so that the archwire slot is oriented for insertion and removal of the archwire in a labio-lingual direction, that is, normal to the bonding pad as shown, or can be angled from normal to the bonding pad as described by Andrews. Alternatively, the bracket body can be positioned so that the archwire slot is oriented for insertion and removal of the archwire in an incisogingival direction, that is, generally parallel to the bonding pad. The remainder of this description assumes the orientation shown in the drawing Figures, with the understanding that the invention can be used in the alternative orientation without limitation.

Figure 2:
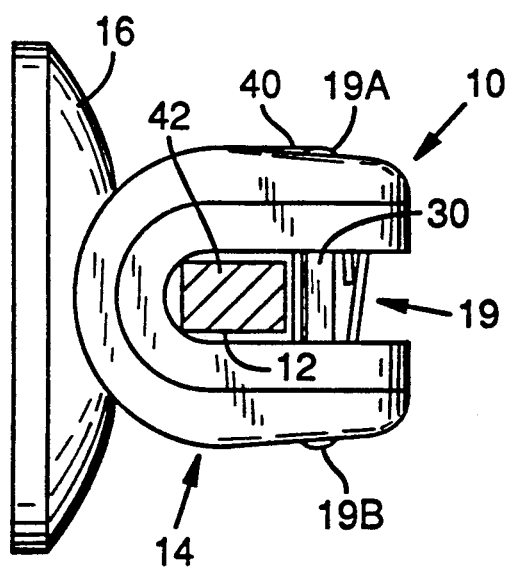
FIG. 2 is an end elevation view, shown to scale, of a bracket according to the invention with an archwire shown in cross section in the archwire slot.
Figure 3:
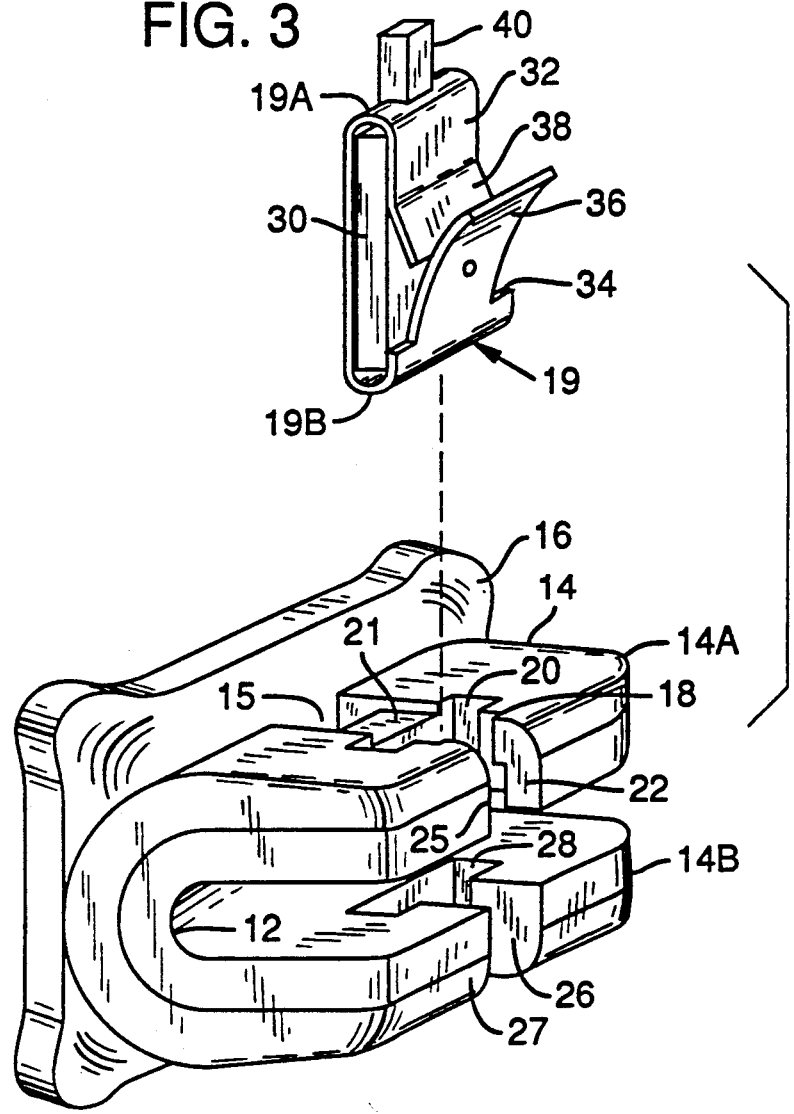
FIG. 3 is a top and endwise exploded perspective view of the bracket of the invention shown with archwire removed.
Figure 4:
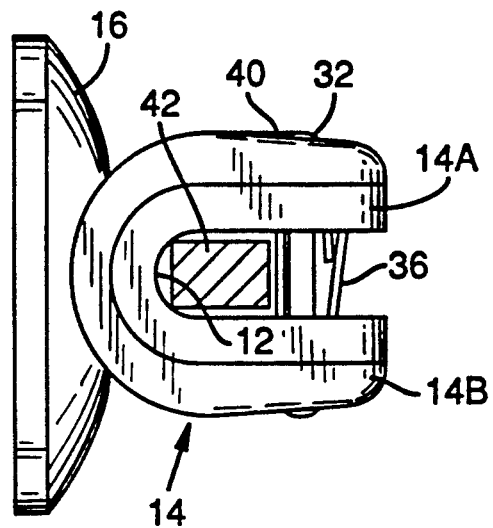
FIG. 4 is a view similar to FIG. 2.

As shown in FIGS. 2 and 3, a closure member or slider 19 fits into an open-ended closure slot 20, 28 and is slidable transversely over the archwire slot 12 to retain the archwire 42 securely in the bracket body. The closure member is generally flat, wide and rectangular in shape, having a first end 19A and a second end 19B.

The closure member is sized to a length such that, when the closure member is closed, the ends 19A, 19B are substantially flush with opposite outer sides of the bracket body. The closure member's shape provides a substantial area of contact between the closure member and the archwire for retaining the archwire in shear. The closure member preferably has a mesiodistal width substantially greater than its thickness (its labio-lingual dimension in the drawing Figures) and substantially greater than the width of the archwire slot. The closure slot preferably has a cross-sectional mesio-distal to labio-lingual aspect ratio of at least 3:1, and more preferably about 5:1. A preferred construction of member 19 is further described below.

Figure 5:
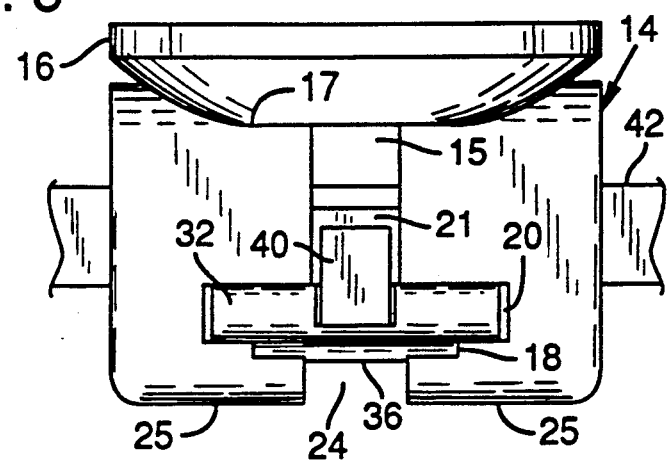
FIG. 5 is a top elevational view of the bracket of FIG. 4.
Figure 7:
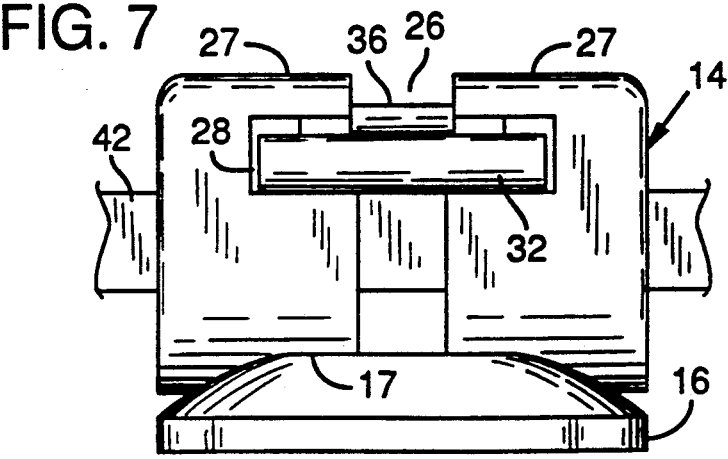
FIG. 7 is a bottom elevational view of the bracket of FIG. 4.
Figure 8:
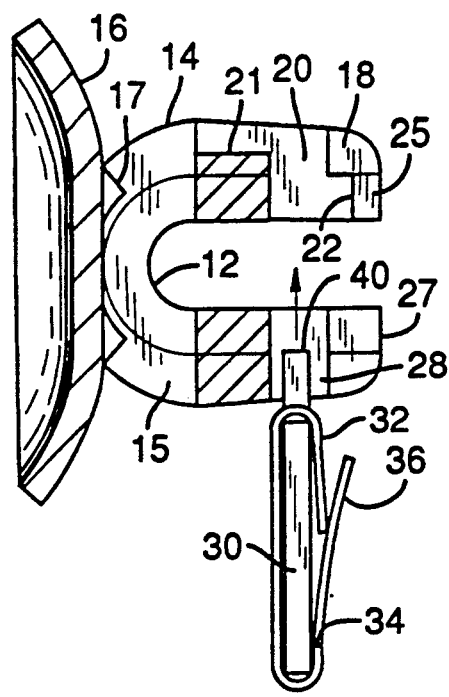
FIG. 8 is a cross-sectional view of the bracket body taken along lines 8—8 in FIG. 6 showing initial insertion of the closure member.
Figure 9:
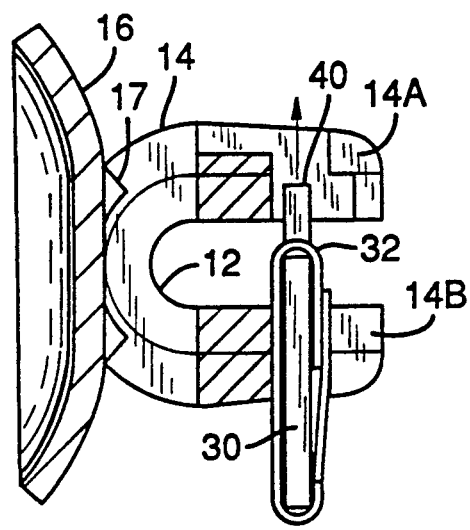
FIG. 9 is a cross-sectional view like FIG. 8 showing further insertion of the closure member.

The closure slot includes a first slot portion 20 formed in the first side portion 14A of the bracket body and a second slot portion 28 formed in the second side portion 14B of the bracket body. As shown in FIGS. 5 and 7, the closure slot is open at opposite outer sides of the bracket body and has a generally T-shaped configuration, including by a central vertical slot portions 24, 26 and horizontal slot portions 20, 28. The closure slot is defined in the first side portion of the bracket body by L-shaped mirror-image arms 25 opposed across slot portion 24 and in the second side portion of the bracket body by L-shaped mirror-image arms 27 opposed across slot portion 26. Vertical slots 24, 26 and closure slot portions 20, 28 are normal to archwire slot 12.

Thus, the closure member and the closure slot portions are arranged so that the closure member can be slid transversely of the archwire slot from an open position (FIG. 11) to a closed position (FIG. 10) through the first slot portion 20. In the open position, the second end 19B of the closure member is retained in the first slot 20, with the archwire slot open for insertion or removal of an archwire 42. In the closed position, the first end 19A of the closure member is retained within the first slot portion 20 and the second end 19B is within the second slot portion to retain the archwire 42 in shear.

Figure 12:
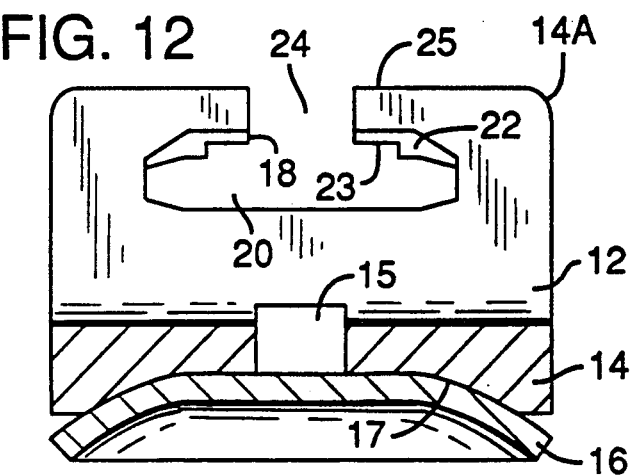
FIG. 12 is a cross-sectional view taken along lines 12—12 in FIG. 6, omitting the archwire and closure member, showing internal structural details of the bracket body.

The bracket body and closure member include first locking means for releasably locking the closure member in the closed position and second locking means for locking the closure member in an open position in the closure slot to insert or remove the archwire, as further described below. More specifically, as shown in FIG. 12, the first side portion 14A of the bracket body includes means defining an internal shoulder 18 (shoulder 18A in FIG. 12A), formed by a recess 22 in arms 25. Shoulder 18 is oriented normal to the direction of closure of the closure member. The closure member 19, in turn, has structure next described for engaging shoulder 18 in the aforementioned open and closed positions.

Figure 10:
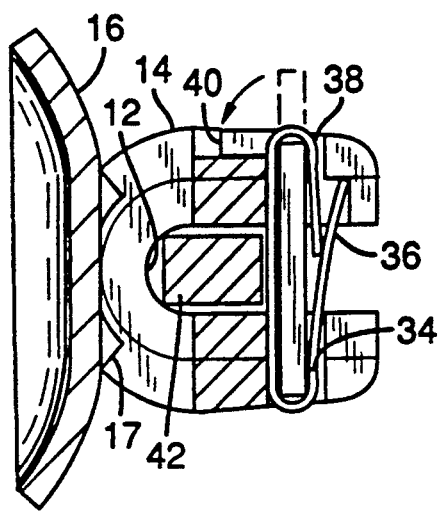
FIG. 10 is a cross-sectional view like FIG. 8 showing full insertion of the closure member and bending of the locking tab.

The closure member 19 shown in FIGS. 2-11 includes a flat core 30 (e.g., 0.006 inch 300 Series full hard stainless steel spring stock) having a flat spring member 32 (e.g., 0.003 inch 300 series stainless) wrapped or folded lengthwise around the core 30. The closure members 119, 219 of FIGS. 20 and 21 omit core 30 and member 219 would usually be of thicker spring stock, e.g., 0.006 inch. In all embodiments, the spring member has a free end 36 and an opposite, inner end 38 which is overlapped by free end 36. Both ends of the spring have a recurved shape so that the free end is biased outward. This arrangement enables the free end 36 to engage the internal shoulder 18 to define the first locking means when the closure member is in the closed position as shown in FIG. 10.

Referring to FIGS. 3 and 8-11, the core 30 of the closure member has an end tab 40, narrower than the remainder of the closure member, protruding through a hole in the spring member. The end tab is bendable downward as shown in FIG. 10 to engage an outer side of the bracket body to retain the closure member in the closed position. This feature provides a stop which prevents the closure member from being retracted when the free end 36 of the spring is engaged against shoulder 18.

Figure 11:
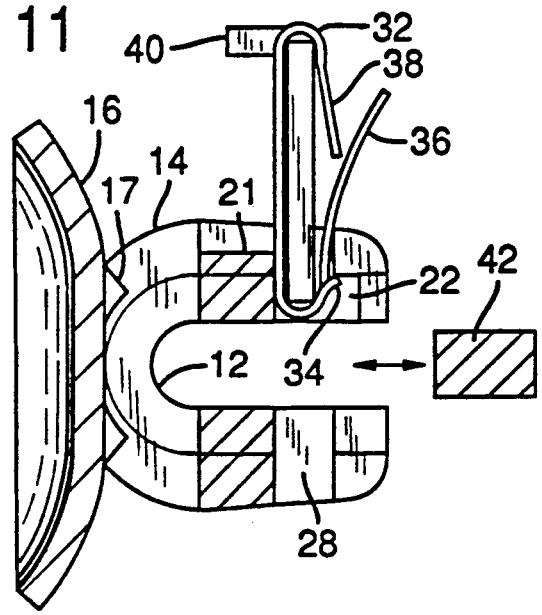
FIG. 11 is a cross-sectional view like FIG. 8 showing removal of the bracket member.

The free end 36 of spring member 32 is narrower than the remainder of the spring, with a pair of transitions or steps on opposite sides of member 32 near the second end 19B forming a pair of intermediate retention ears 34, best seen in FIGS. 3 and 11. This feature serves two purposes. First, referring to FIG. 12, the closure slot portion 20 has an upper wall which includes a pair of mirror-symmetric recesses or stair steps 23 spaced to a width slightly greater than the width of the free end but narrower than the width of the remainder of the closure member. This arrangement provides an escape notch for releasing the locked free end when it is depressed by the orthodontist. Second, the ears 34 are wider than the escape notch so they cannot pass through it and are positioned lengthwise of the closure member so as to engage the internal shoulder 18 when the closure member is in the open position, thereby defining the second locking means. The lengthwise position of the ears 34 and the depth of recess 22 are arranged so that the second end 19B is clear of the archwire slot when the closure member is in the open position as shown in FIG. 11. Also, while the closure member is in the open position, the free end 36, being biased out of the plane of the closure slot, engages arms 25 at an angle to resist inadvertent closure while the archwire is removed. This feature provides a third, frictional or resilient locking means for resisting movement of the closure member from the open to closed positions.

Figure 12A:
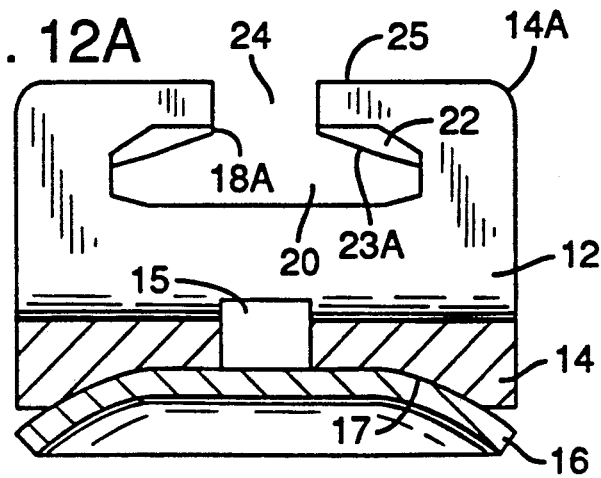
FIG. 12A is a view like FIG. 12 showing an alternative form of internal shoulder and escape notch.

Referring to FIG. 12A, shoulder 18 can alternatively be formed with an upper wall formed by a pair of mirror-symmetric ramps 23A, rather than steps 23 as in FIG. 12. The ramps 23A can be used because the spring 32 gives some leeway in tolerances of fit. An advantage of this embodiment is that it self-centers the closure member 19 in open, closed and transitory positions.

Figure 6:
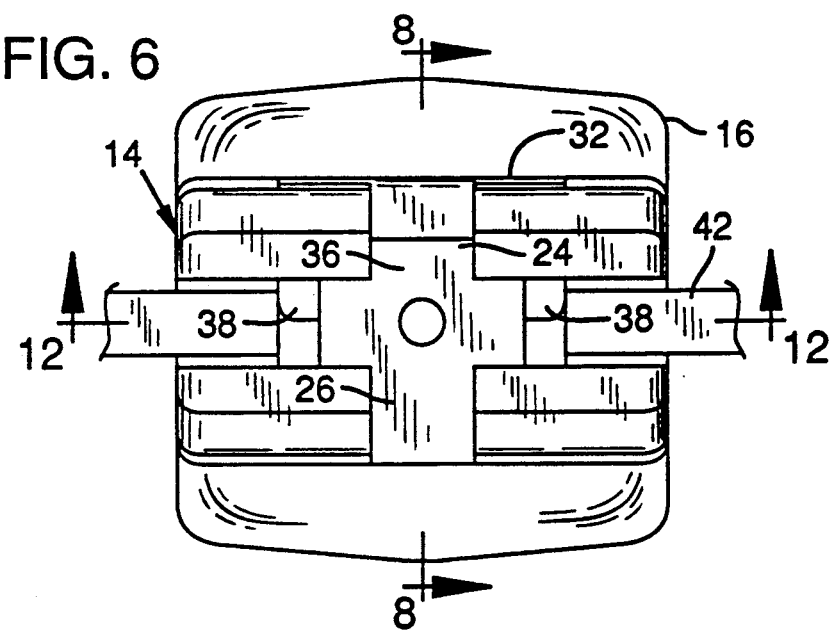
FIG. 6 is a front plan view of the bracket of FIG. 4.

As shown in FIGS. 2-11, the bracket body 14 has a generally rectangular external profile which is continuous, i.e., unbroken by wings or other structure. The outer opposite sides of sidewalls 14A, 14B are substantially flat and nearly parallel to the archwire slot 12, preferably with a slight outward taper proceeding from top (archwire slot entrance) to bottom (base portion connected to pad 16). The opposite end faces of the bracket are also parallel or slightly tapered, as best seen in FIGS. 5 and 7. The bracket body also has a generally rectangular plan view profile, slightly rounded at the corners, as shown in FIG. 6. The bracket body thus has a substantially constant or slightly tapered cross section.

Figure 13:
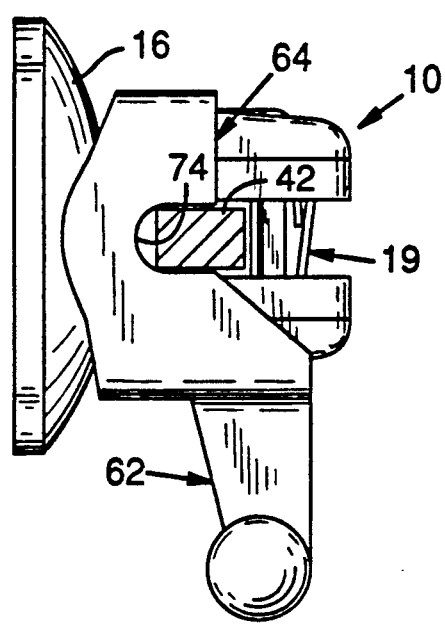
FIGS. 13-15 show elevation and plan views of an auxiliary sleeve attachment for use with the bracket of FIGS. 2-12.
Figure 14:
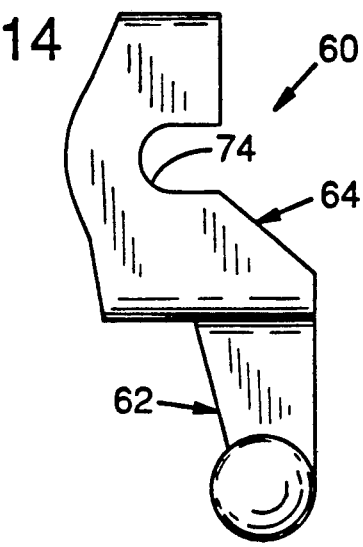
Figure 15:
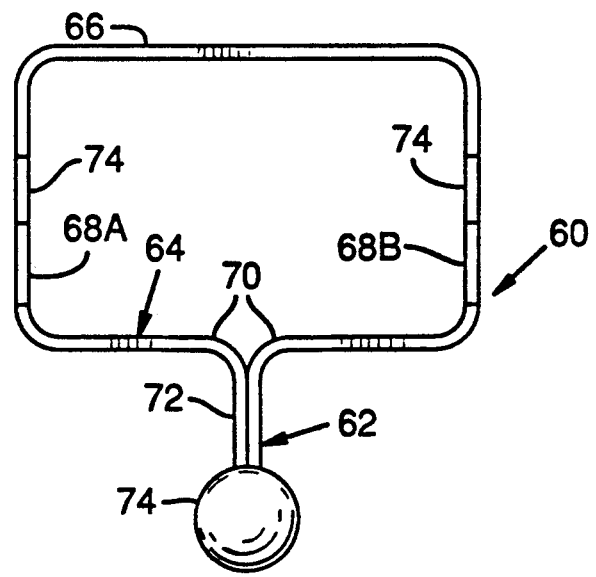

Referring to FIGS. 13-15, an auxiliary attachment 60 has a hook or knob 62 carried on a collar 64 formed into a generally rectangular shape with rounded corners to fit conformably over the bracket body 14. The collar 64 is a flat metal (stainless steel) strip formed into a closed loop of rectangular shape, defined by a continuous back wall, opposite sidewalls 68A, 68B, and a front wall 70. The hook is formed by coupling end portions of the metal strip side by side to form a double-thickness arm 72 protruding outward at a right angle from the center of the front wall and spherical knob 62 is affixed to the end of arm 72. Sidewalls 68A, 68B are mirror images of one another, each including a notch 74 located to align with the base of the archwire slot 12.

Referring to FIGS. 16 and 17, it is presently preferred to make the bracket body depicted herein by the method described in my U.S. patent application Ser. No. 07/247,178, filed Sept. 21, 1988, now U.S. Pat. No. 5,018,259. This method can also be used to make the auxiliary attachment 60. Other known methods, however, may be adapted to make the bracket body.

FIG. 16 shows one segment 80, of a strip of similar segments of a thin sheet of metal 0.014 inch 17/7 stainless steel), patterned in flat condition symmetrically about centerline CL to define the inner layer of sidewalls 14A, 14B. The portion of segment 80 between dimension lines 82, 84 forms the inner layer. The remaining portions are end tabs containing alignment pin holes 86 used in assembly of the bracket body. After assembly, the tab portions are cut off along dimension lines 82, 84.

FIG. 17 shows one segment 90 similarly patterned to define the outer layer of the bracket body sidewalls 14A, 14B, the corresponding dimension lines and alignment holes being indicated by like reference numerals. Reference numerals matching those used in FIGS. 2-12 are also shown in FIGS. 16 and 17 to correlate the features of the patterned segments with the previously-described structure of the assembled bracket body. Dimensions are also shown in FIGS. 16 and 17 for an operative example of a bracket 10 which has been successfully made and tested. Arrows 88 indicate the preferred grain orientation of the sheet metal used to fabricate these parts.

In both FIGS. 16 and 17, closure slot portions 20 and 28 are indicated, as are vertical slot portions 24, 26. Generally rectangular openings 15A, 15B in the two segments align in the assembled bracket body to form slot 15 in the base of body 14 which enables the bracket to be engaged by the orthodontist. The region designated by a bracket at reference numeral 12 in FIG. 16 indicates the portion of segment 80 which, when folded into a U-shape, forms the archwire slot. The oblong recess 17 in the bracket body base is formed by half-etched regions 17A, 17B in the outer surface of segment 90. Another half-etched square region 21 forms a recess in the outer side of sidewall 14A for receiving the closure member tab 40 when the tab is bent over as shown in FIG. 10.

The closure slot portion 20 in segment 90 (FIG. 16) is patterned to form what become symmetrical recesses 22 on opposite sides of slot 24. Internal shoulder portions 18 are symmetrically formed in segment 90 in alignment with recesses 22 for engagement by either the free end 36 of the closure member or intermediate ears 34. The shoulder portions are notched symmetrically on both sides of slot 24 to form the escape notch 23 for releasing the free end when depressed by pressure exerted through vertical slot 24.

Figure 18:
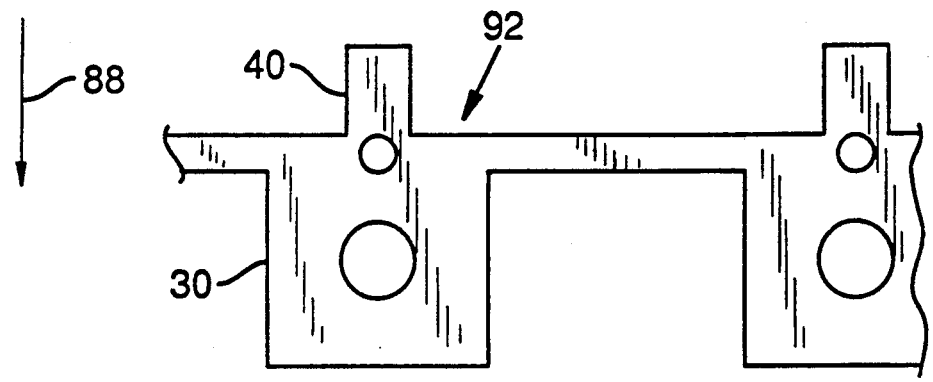
FIG. 18 is a plan view of the patterned layer forming a slider core of the slider assembly of FIG. 2.
Figure 19:
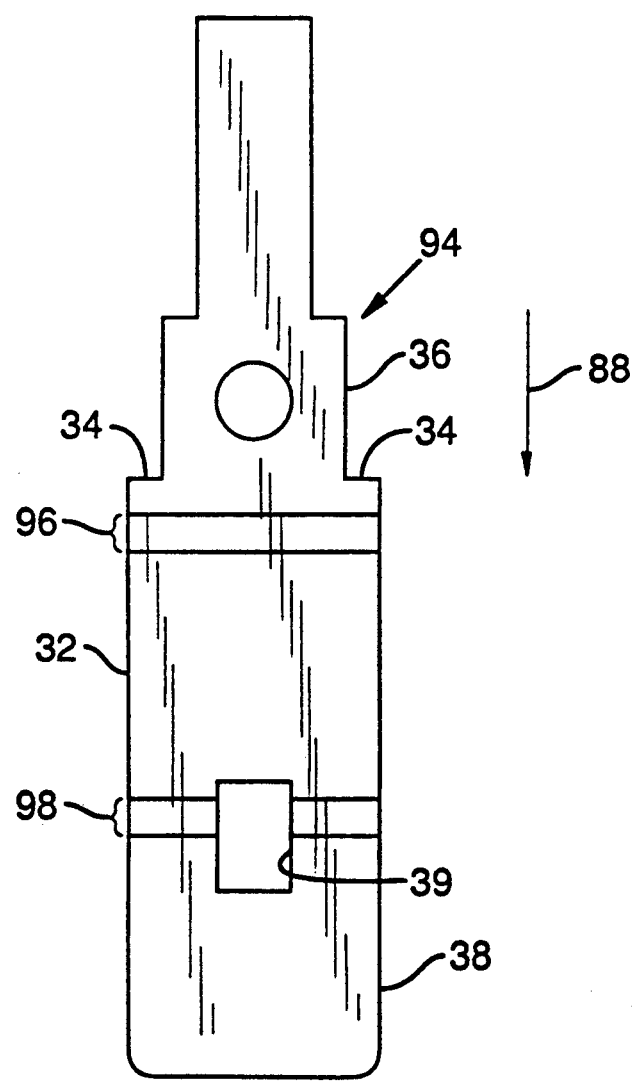
FIG. 19 is a plan view of the patterned, unformed layer forming a pressure spring of the closure assembly of FIG. 2.

FIG. 18 shows the fabrication of core member 30 with tab 40 as a segment 92 in a strip of such segments patterned by etching or stamping. FIG. 19 shows a segment 94 forming the spring member 32 in flat condition, similarly patterned symmetrically about centerline CL to define the intermediate ears 34, the narrow free end 36, inner end 38, and a rectangular hole 39 for tab 40 to extend through the spring member. Brackets 96, 98 indicate narrow transverse bending zones about which segment 94 is bent to wrap it lengthwise around core 30 to form closure member 19.

Figure 20:
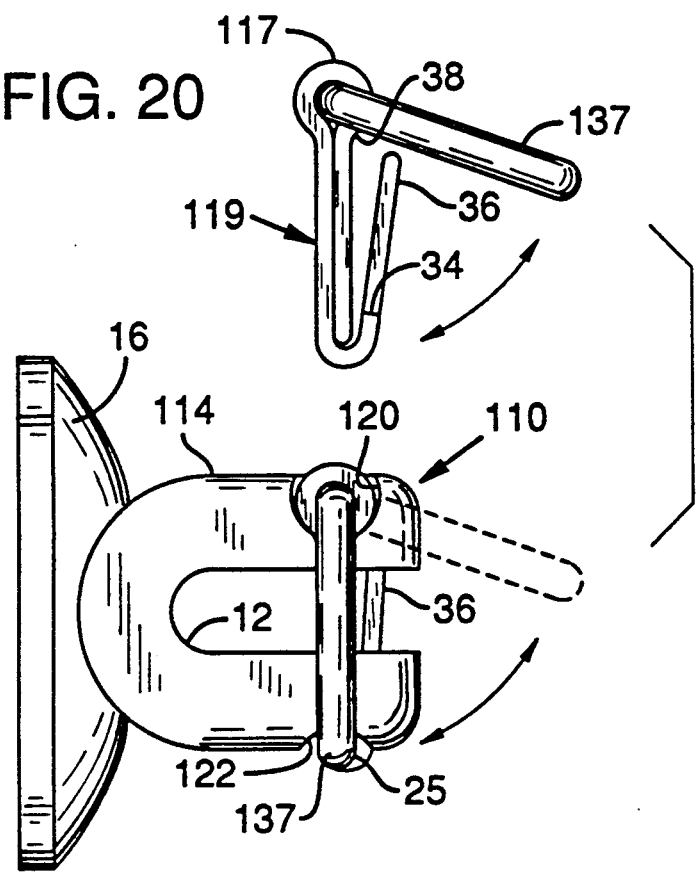
FIG. 20 is a view similar to FIG. 2 showing a first alternative embodiment of ligatureless archwire slot closure usable in the present invention.

FIG. 20 shows an alternative form of bracket 110 having a body 114 and closure member 119 arranged for securing by means of a bale 137. The bale is a rectangular wire loop pivotally connected to the first end of closure member 119 by means of a cylindrical fold 117 in end portion 38A of the spring member. The spring member preferably still includes the free end 36 and intermediate ears 34 described above. The bracket body 114 is generally similar to bracket body 14 but has semicircular notches 120, 122 on its opposite outer sides so that fold 117 and an opposite, parallel section of bale 137 can be received in the notches and be partially recessed within the sidewalls of the bracket body. When the closure member is closed, the bale serves essentially the same purpose as tab 40 in locking the closure member in the closed position. The core member 30 and tab 40 are thus omitted in this embodiment. The bale also provides a useful handle for the orthodontist to manipulate the closure member.

Figure 21:
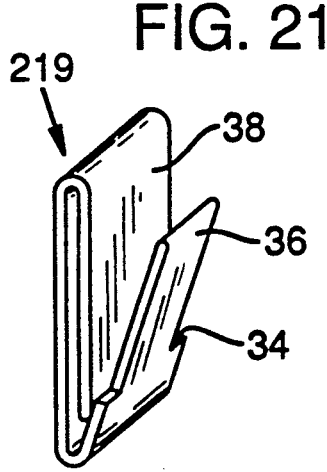
FIG. 21 is a perspective view similar to FIG. 2 showing a second alternative embodiment of ligatureless archwire slot closure usable in the present invention.

FIG. 21 shows a further alternative embodiment of the closure member 219. As mentioned above, this embodiment is like member 19 but leaves out core member 30 and tab 40 and uses a somewhat thicker sheet of spring material. This embodiment is best used in a bracket wherein the outer end of the second portion of the closure slot is, or can be, closed to retain closure member 219 in the locked position. For example, if the bracket body is mounted with sidewall 14B lying on a pad, so that the archwire slot is parallel to the pad, slot portion 28 is closed. Core member 30 with tab 40 is again unneeded because the closed slot portion 28 will retain member 219 in the closed position. The closure member 219 is ordinarily inserted into the closure slot via soot portion 20, which will be in a labio-lingual direction when the bracket is mounted on a tooth.

Having described and illustrated the principles of the invention in a preferred embodiment thereof, it should be apparent that the invention can be modified in arrangement and detail without departing from such principles. I claim all modifications and variation coming within the spirit and scope of the following claims.

I claim:

1. A self-locking orthodontic bracket mountable on a tooth, the bracket comprising:
   a bracket body having first and second side portions spaced apart to define an archwire slot for receiving an archwire;
   a closure slot extending transversely of the archwire slot in the bracket body;
   a closure member receivable within the closure slot and slidable across the archwire slot;
   the closure slot including a first slot portion formed in the first side portion of the bracket body an a second slot portion formed in the second side portion of the bracket body on opposite sides of the archwire slot so that the closure member can be slid to a closed position through the first slot portion transversely of the archwire slot with an end portion inserted into the second slot portion to retain the archwire in the archwire slot;
   first locking means for releasably locking the closure member in said closed position in the closure slot; and
   second locking means for locking the closure member in an open position in the closure slot to insert or remove the archwire;
   the first slot portion including means defining an internal shoulder oriented normal to the direction of closure of the closure member; and
   the closure member including a folded flat spring member having a free end biased outward to engage the internal shoulder to define said first locking means when the closure member is in the closed position.

2. A bracket according to claim 1 including third, frictional locking means for resisting movement of the closure member between the open and closed positions.

3. A bracket according to claim 2 in which the frictional locking means includes a portion of the folded flat spring member biased against a wall of the first slot portion.

4. A self-locking orthodontic bracket mountable on a tooth, the bracket comprising:
   a bracket body having first and second side portions spaced apart to define an archwire slot for receiving an archwire;
   a closure slot extending transversely of the archwire slot in the bracket body;
   a closure member receivable within the closure slot and slidable across the archwire slot;
   the closure slot including a first slot portion formed in the first side portion of the bracket body and a second slot portion formed in the second side portion of the bracket body on opposite sides of the archwire slot so that the closure member can be slid to a closed position through the first slot portion transversely of the archwire slot with an end portion inserted into the second slot portion to retain the archwire in the archwire slot;
   first locking means for releasably locking the closure member in said closed position in the closure slot; and
   second locking means for locking the closure member in an open position in the closure slot to insert or remove the archwire;
   the first slot portion including means defining an internal shoulder oriented normal to the direction of closure of the closure member; and
   the closure member including a folded flat spring having a free end biased outward and an intermediate retention ear positioned to engage the internal shoulder to define said second locking means when the closure member is in the open position.

5. A self-locking orthodontic bracket mountable on a tooth, the bracket comprising:
   a bracket body having first and second side portions spaced apart to define an archwire slot for receiving an archwire;
   a closure slot extending transversely of the archwire slot in the bracket body;
   a closure member receivable within the closure slot and slidable across the archwire slot;

the closure slot including a first slot portion formed in the first side portion of the bracket body and a second slot portion formed in the second side portion of the bracket body on opposite sides of the archwire slot so that the closure member can be slid to a closed position through the first slot portion transversely of the archwire slot with an end portion inserted into the second slot portion to retain the archwire in the archwire slot;

first locking means for releasably locking the closure member in said closed position in the closure slot; and second locking means for locking the closure member in an open position in the closure slot to insert or remove the archwire;

the first slot portion including means defining an internal shoulder oriented normal to the direction of closure of the closure member; and the closure member including a folded flat spring having a free end biased outward to engage the internal shoulder to define said first locking means when the closure member is in the closed position and an intermediate retention ear positioned to engage the internal shoulder to define said second locking means when the closure member is in the open position.

6. A self-locking orthodontic bracket mountable on a tooth, the bracket comprising:

a bracket body having first and second side portions spaced apart to define an archwire slot for receiving an archwire;

a closure slot extending transversely of the archwire slot in the bracket body;

a closure member receivable within the closure slot and slidable across the archwire slot;

the closure slot including a first slot portion formed in the first side portion of the bracket body and a second slot portion formed in the second side portion of the bracket body on opposite sides of the archwire slot so that the closure member can be slid to a closed position through the first slot portion transversely of the archwire slot with an end portion inserted into the second slot portion to retain the archwire in the archwire slot;

first locking means for releasably locking the closure member in said closed position in the closure slot; and second locking means for locking the closure member in an open position in the closure slot to insert or remove the archwire;

the closure member including a flat core member and flat spring member wrapped lengthwise around a portion of the core member, the core member having an end protruding through the spring member and bendable downward to engage an outer side of the bracket body to retain the closure member in the closed position.

7. A bracket according to claim 6 in which:

the first slot portion includes means defining an internal shoulder oriented normal to the direction of closure of the closure member; and the spring member includes a free end biased outward to engage the internal shoulder to define said first locking means when the closure member is in the closed position;

the core member end protruding through the spring member being bent downward to engage an outer side of the bracket body to retain the closure member in the closed position.

8. A self-locking orthodontic bracket mountable on a tooth, the bracket comprising:

a bracket body having first and second side portions spaced apart to define an archwire slot for receiving an archwire;

a closure slot extending transversely of the archwire slot in the bracket body;

a closure member receivable within the closure slot and slidable across the archwire slot;

the closure slot including a first slot portion formed in the first side portion of the bracket body and a second slot portion formed in the second side portion of the bracket body on opposite sides of the archwire slot so that the closure member can be slid to a closed position through the first slot portion transversely of the archwire slot with an end portion inserted into the second slot portion to retain the archwire in the archwire slot;

first locking means for releasably locking the closure member in said closed position in the closure slot; and second locking means for locking the closure member in an open position in the closure slot to insert or remove the archwire;

the first and second locking means including means defining an internal shoulder extending along one side of he archwire slot and oriented across a side of the closure slot normal to the direction of closure of the closure member;

the first locking means including a free end of a flat spring member biased to engage the internal shoulder in said closed position, the free end having a width less than a width of the closure slot, and the internal shoulder including means defining an escape notch in the internal shoulder for releasing the free end when depressed.

9. A bracket according to claim 8 in which the escape notch includes a mirror-symmetric pair of steps spaced to slightly greater than the width of the free end.

10. A bracket according to claim 8 in which the escape notch includes a mirror-symmetric pair of ramps spaced to permit release of the free end.

11. A self-locking orthodontic bracket mountable on a tooth, the bracket comprising:

a bracket body defining an archwire slot oriented for insertion and removal of an archwire in a labio-lingual direction normal to a bonding pad;

a closure slot extending transversely of the archwire slot in the bracket body; and a closure member, having first and second ends, receivable in and slidable occluso-gingivally within the closure slot;

the closure slot including a first slot portion formed in a first side of the bracket body and a second slot portion formed in a second side of the bracket body on opposite sides of the archwire slot so that the closure member can be slid through the first slot portion across the archwire slot and inserted into the second slot portion to retain the archwire in shear;

the closure slot having a generally flat, rectangular shape including a width substantially greater than a thickness thereof;

the closure member being formed by a flat folded spring member rectangularly shaped and sized to fit conformably within the rectangular shape of the closure slot.

12. A bracket according to claim 11 in which the first and second portions of the closure member are defined by opposite end portions and the closure member is sized to a length such that, when the closure member is closed, the end portions are substantially flush with opposite outer sides of the bracket body.

13. A bracket according to claim 11 in which the closure slot and closure member have a cross-sectional aspect ratio of at least 3:1.

14. A bracket according to claim 11 in which the closure slot and closure member have a cross-sectional aspect ratio of about 5:1.

15. A self-locking orthodontic bracket mountable on a tooth, the bracket comprising:
 a bracket body defining an archwire slot of a predetermined width for receiving an archwire;
 a closure slot extending transversely of the archwire slot in the bracket body; and
 a closure member, having first and second ends, receivable and slidable within the closure slot;
 the closure slot including a first slot portion formed in a first side of the bracket body and a second slot portion formed in a second side of the bracket body on opposite sides of the archwire slot so that the closure member can be slid through the first slot portion across the archwire slot and inserted into the second slot portion to retain the archwire in shear;
 the closure slot having a generally flat, rectangular shape including a width substantially greater than the width of the archwire slot;
 the closure member being formed by a flat folded spring member rectangularly shaped and sized to fit conformably within the rectangular shape of the closure slot.

16. A bracket according to claim 15 in which the closure slot includes means defining an internal shoulder extending along one side of the archwire slot and oriented across a side of the closure slot normal to the direction of closure of the closure member and the flat folded spring member includes means positioned to engage the internal shoulder when the closure member is in at least one of an open and closed position to releasably lock the closure member in said position.

17. A bracket according to claim 15 in which the bracket body has walls of substantially constant thickness formed into a U-shaped cross section to form the side portions that define said archwire slot.

18. A self-locking orthodontic bracket mountable on a tooth, the bracket comprising:
 a bracket body having first and second side portions spaced apart to define an archwire slot oriented for receiving an archwire in a labio-lingual direction;
 a closure slot extending transversely of the archwire slot in the bracket body;
 a closure member receivable within the closure slot and slidable across the archwire slot;
 the closure slot including a first slot portion formed in the first side portion of the bracket body and a second slot portion formed in the second side portion of the bracket body on opposite sides of the archwire slot so that the closure member can be slid to a closed position through the first slot portion across the archwire slot with an end portion inserted into the second slot portion to retain the archwire in the archwire slot;
 the bracket body having an external profile which is substantially continuous and the closure member having a generally flat, rectangular shape and end which are positioned substantially flush with the sides of the body when received in the closure slot in the closed position;
 the bracket body having walls of substantially constant thickness formed into a U-shaped cross section to form the side portions that define said archwire slot.

19. A bracket according to claim 18 in which a central outer portion of said walls is recessed to received a bonding pad, thereby positioning the archwire slot close to the bonding pad.

20. A bracket according to claim 18 in which the closure slot is open at opposite outer sides of the bracket body.

21. A bracket according to claim 20 in which the closure member includes means for retaining the closure member in a closed position.

22. A bracket according to claim 18 including an auxiliary attachment mounted on a collar closely conforming to the profile of the bracket body so as to be placed on or removed from the bracket without removing the closure member.

23. A bracket according to claim 22 in which the bracket body profile is approximately rectangular and the collar has a rectangular shape conforming to said profile.

24. A self-locking orthodontic bracket mountable on a pad arranged for mounting on a tooth, the bracket comprising:
 a bracket body having first and second side portions spaced apart to define an archwire slot for receiving an archwire;
 a closure slot extending transversely of the archwire slot in the bracket body;
 the closure slot extending through the first and second side portions of the bracket body;
 a flat, rectangular closure member, having first and second ends, receivable and slidable within the closure slot;
 the closure slot and closure member being mutually arranged so that the closure member can be slid through the closure slot across the archwire slot to a closed position in which the first and second ends thereof are secured within the first and second side portions, respectively, to retain the archwire in shear;
 the closure member being formed by a flat folded spring member rectangularly shaped and sized to fit conformably within the rectangular shape of the closure slot.

25. A bracket according to claim 24 in which the bracket body has an external profile defined by flat opposite outer sides substantially parallel to the archwire slot and the closure member is sized to a length approximately equal to a spacing between said outer sides so that the ends of the closure member are substantially flush with the outer sides when the closure member is closed.

26. A bracket according to claim 24 in which the closure member includes a bale swingably connected to one end thereof and sized to extend around the bracket body when closed.

27. A bracket according to claim 26 in which the bracket body has notches on opposite outer sides for receiving the bale.